United States Patent [19]

Gormley

[11] Patent Number: 4,569,358
[45] Date of Patent: Feb. 11, 1986

[54] OPTICAL MICROMETRY OF SKIN SURFACES

[76] Inventor: Daniel E. Gormley, 412 W. Carroll, #207, Glendora, Calif. 91740

[21] Appl. No.: 663,428

[22] Filed: Oct. 22, 1984

[51] Int. Cl.⁴ .................................................. A61B 5/10
[52] U.S. Cl. ..................................... 128/774; 356/376
[58] Field of Search ............... 128/774, 776, 777, 779, 128/630, 1 R, 653, 655; 356/376; 264/299

[56] References Cited

U.S. PATENT DOCUMENTS 4,355,904 10/1982 Balasubramanian ................ 356/376
4,502,785 3/1985 Truax ................................... 356/376

Primary Examiner—Kyle L. Howell
Assistant Examiner—C. J. Graczy
Attorney, Agent, or Firm—Boniard I. Brown

[57] ABSTRACT

A series of casts are taken of a skin surface over a period of time and then measured by means of an automatically focusing microscope to produce a quantitative model of the changes in the topology of the surface.

10 Claims, 7 Drawing Figures

FIG-1
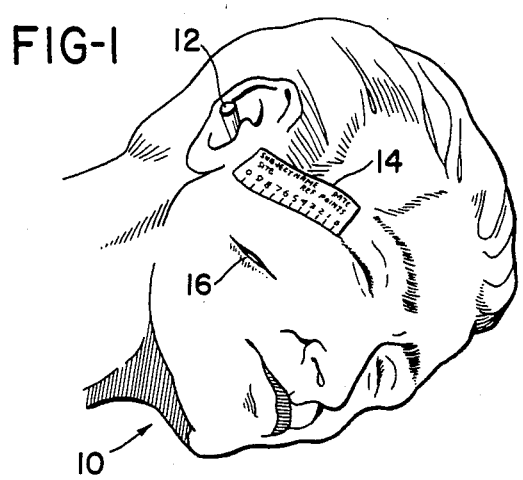
FIG-2
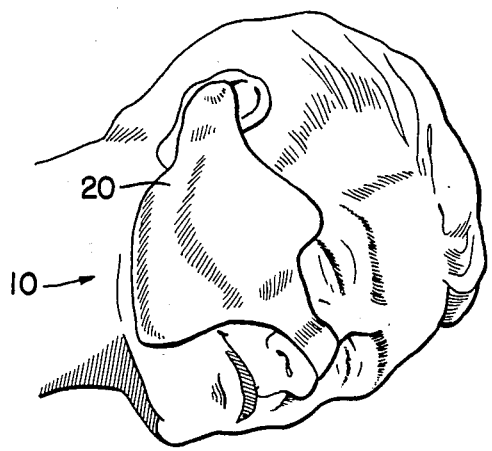
FIG-3
FIG-4
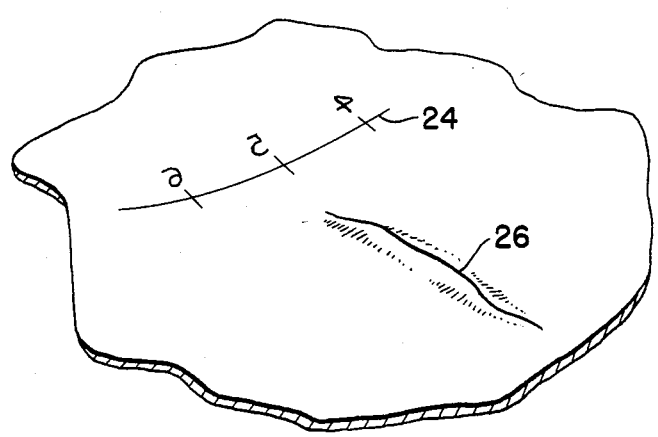

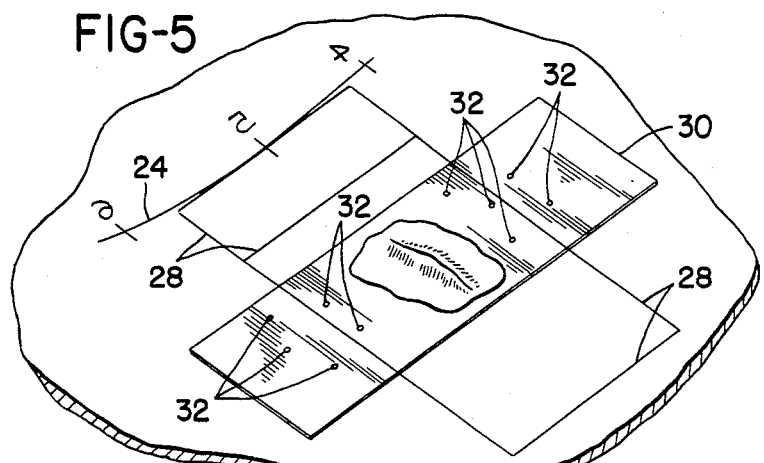
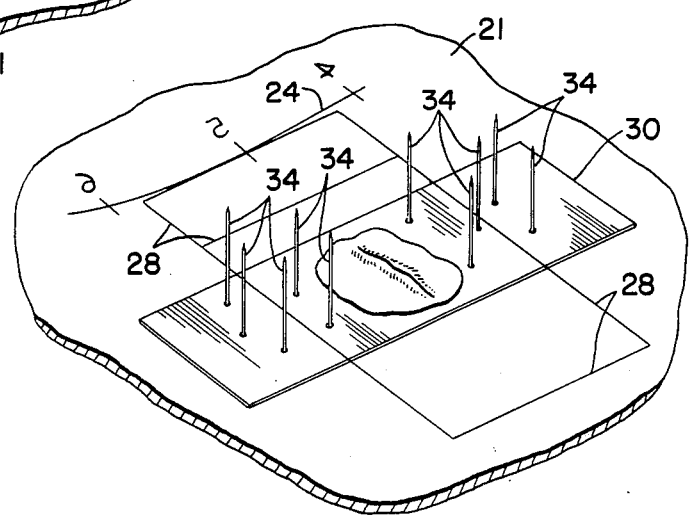
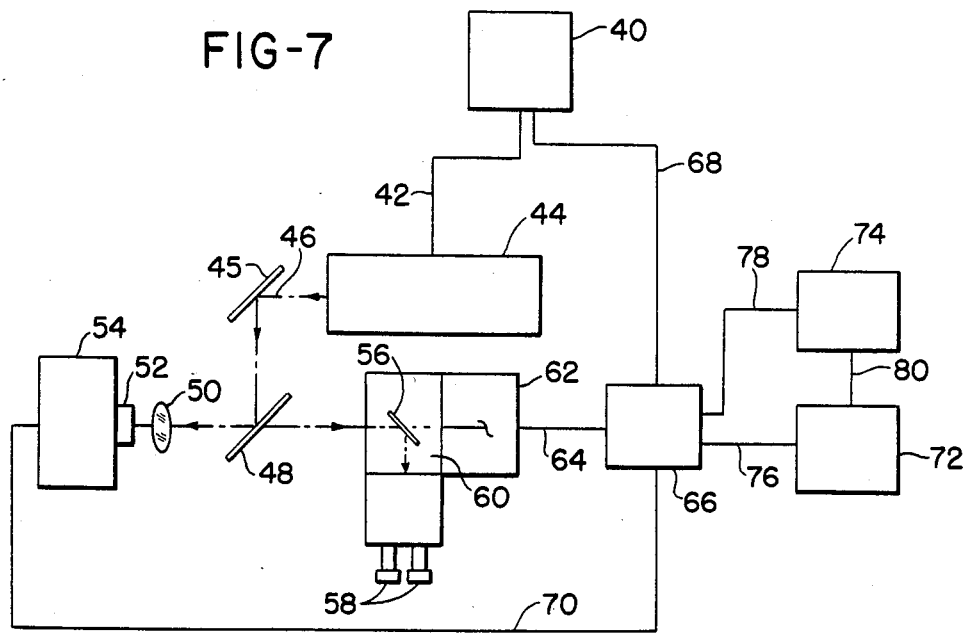

OPTICAL MICROMETRY OF SKIN SURFACES

BACKGROUND OF THE INVENTION

This invention relates to methods for measuring changes in the topology of a skin surface over time.

There are a variety of fields in which it is important to measure the changes in the topology of a surface over time. One such application is in the medical field in which surface qualities of the skin need to be defined in terms of reproducible measurements in order to make objective quantitative assessments of surface-altering therapeutic treatments. Most quantitative studies of biological surfaces are done with silicon rubber, acrylic, or plaster replicas of the surfaces. Such substances provide accurate three-dimensional contour models that are convenient to measure and store. Techniques developed for the measurement of these models have used one of two basic approaches: mechanical tracings can be obtained by passing a stylus over the studied surface or techniques using light reflection can be used.

SUMMARY OF THE INVENTION

Changes in the topology of a skin surface are measured by first forming a dimensionally stable first replica of the topology of the skin surface at a first time, the replica being referenced to at least two stable anatomic locations on the skin surface, then forming further replicas of the topology of the skin surface, at least one later time also referenced to the at least two stable anatomic locations and finally measuring dimensional differences between the first and further replicas with the replicas commonly referenced such that a quantitative model of the changes in the topology of the skin surface may be made. Such models can include analysis of the relative roughness or smoothness of the surface by statistical techniques and also volumetric changes as between a given feature location on the surface taken at different times. The process is particularly adapted to analyzing relatively small areas of skin surface in very fine detail by automatic methods.

Basically, casts are made of cutaneous surfaces with a medical grade silastic elastomer which poured in a semiliquid state onto the studied surfaces in a relatively thin layer. The elastomer polymerizes to form a silicon rubber cast. These casts are dimensionally accurate in comparison to the originals to within a tolerance of about one micron. Stable anatomic reference points are used as the basis for a system of coordinates from which further measurements may be made. These coordinates can be employed in conjunction with templates to ensure that corresponding areas of casts obtained at different times are correctly measured. The measurements themselves are most conveniently carried out by an automatically focusing microscope which is set up to automatically take and record values at selected points on a grid covering the area of interest on the surface. The output of the microscope will record the position of the skin surface relative to an arbitrary coordinate system, producing X, Y, and Z coordinate system values for each measured point on the skin surface. These data may then be operated upon by a variety of different algorithms and statistical processing techniques to produce the particular quantitative assessment of the skin surface changes which is desired. One such analysis is a regional analysis which is accomplished by making measurements along multiple lines passing through the study area. The measured points are then subjected to statistical analysis in which a linear least regression analysis is done and the standard error of all the measured points about the line of best fit is computed to achieve an index of the "roughness" of the surface. Volumetric analysis may also be done by using the data obtained to compute the volume changes of a surface feature, for instance a scar, before and after a treatment.

BRIEF DESCRIPTION OF THE DRAWINGS

FIG. 1 is an isometric view of patient in the initial preparation step for forming a skin surface cast;

FIG. 2 is an isometric view showing the poured and solidified cast in situ;

FIG. 3 is an isometric view of a portion of the removed cast showing the mirror image transfer of the reference tape and the skin surface feature of interest;

FIG. 4 is an enlarged isometric view of a portion of the removed cast.

FIG. 5 is an isometric view of the cast showing a preparatory step for the establishment of a repeatable reference grid;

FIG. 6 is an isometric view of the cast showing the referenced cast being placed upon a needle jig; and FIG. 7 is a block diagram showing the functional elements of the automatically focusing microscope.

DETAILED DESCRIPTION OF THE INVENTION

The following detailed description of the invention is directed towards a specific embodiment in which relatively small casts of a skin surface are analyzed by an automatically focusing microscope means. Due to the focal limitations of the microscope, the sizes of the various casts taken over the various time intervals are necessarily rather limited in size. Nevertheless, it should be realized that the method of this invention should not be limited to a mandatory use of the automatically focusing microscope with its attendant limitations and that other measurement means capable of providing accurate X, Y, Z coordinate values for the measured points on the surfaces may be utilized. In any event, the discussion below will be directed towards the use of the microscope means and other steps particularly directed towards measuring relatively small areas of skin surface on a patient's face.

The first step is that of making a silastic elastomer cast or replica of the study surface as shown in FIGS. 1 and 2. Medical grade elastomer is normally used in this process. Similar materials have been used to make dental impressions and casts of cutaneous and industrial surfaces. Concurrently, if meaningful measurements of a given area on a study surface of a patient 10 are to be made, it is essential that a system of coordinates be used which will remain the same for casts which are taken of a given area at different points in time. A basic set of coordinates is established by running a measured tape 14 between two stable reference points on the surface. In the case of studies made of human skin, a tape is run between two stable anatomic reference points such as the outer canthus (corner) of the eye and the attachment of the ear lobe. The markings on the tape are made with ink which is readily transferrable to the silastic rubber cast 20 which will be applied thereover. The surface of the skin is gently cleansed with a 70% isopropyl alcohol solution. The study surface is then placed in a level position and the semiliquid silastic elastomer is poured onto the surface and onto the reference tape 14. The elastomer is also poured onto stable anatomic features such as the nose and the external ear, with care being taken to avoid getting the elastomer into any body orifice. The ear plug 12 prevents entry of the elastomer into the ear.

Once the elastomer has polymerized, a form fitting mold 20 of the subject surface including the feature of interest 16 is created. The three dimensional contours incorporated into the cast can serve as additional reference points and as a device for orienting the cast when it is placed back onto the subject. Pouring the elastomer onto a horizontal surface serves to eliminate shearing and wrinkling forces caused by gravity that might distort the features being studied. The elastomer is poured over the study area to a thickness of about 3 millimeters in order to avoid pressure deformity of the underlying surface. However, for reinforcement, it may be desirable to make a thicker pour in areas away from the study area. Polymerization normally occurs in about two to ten minutes. Additional reinforcement may be obtained by applying plaster of paris to the outside of the silastic elastomer cast before it is removed from the subject. The cast which is removed as shown in FIGS. 3 and 4 provides an accurate form-fitting three dimensional negative model of the surface to which it was applied. The inscriptions transferred in the mirror image fashion shown in FIG. 3 in their entirety as 22 and in FIG. 4 as the fragment 24 from the reference tape 14 to the surface of the replica provide a basic coordinate system which can be further refined. The feature 16 is transferred as a negative impression 26.

In order for meaningful measurements to be made, it is necessary to establish a coordinate system which makes it possible to return with a high degree of accuracy to corresponding areas of replicas made at different times. Only in this way can comparisons be made of the same surface area in order to quantitatively measure the results of surface altering events and treatments to the feature of interest 16. Several different techniques may be utilized to achieve this repeatability and coordinate systems.

In many cases it may be sufficient to establish the coordinate system directly from the markings transferred from the tape as discussed above as shown in FIGS. 5 and 6 on the portion 21 of the cast. Perpendicular lines 28 may be drawn from the reference tape line 24 and used as the basis for defining a rectangular area of study. When more precision is necessary, another method may be used in which a needle jig is created. To do so, the first step is to create a basic outline of the outer boundary of the study area and then to mark several permanent features within the study area with small dots 32. Such features might be any orifices, pits, scars, rills, bifurcations and wrinkles or the like which will be relatively permanent during the course of the study. A transparent sheet of tape 30 is then placed over the marked area of study and then 300 micron diameter needles 34 are inserted through the tape into the marked areas of the cast. The needles 34 and the tape 30 are then removed and the tape which is now punctured by the needles serves as a template for the construction of a jig which is utilized to line up with the same permanent features in subsequent casts taken of the same surface area.

Another technique to establish a reproducible coordinate system as between casts taken at different times of a portion of a skin surface is to utilize a method which may be called the insert cast technique. In this method a first mold or replica is made of the study area and its peripheral boundaries. This large mold may be called a mother cast. The portion of the mother cast which comprises the study area is then carefully cut out. This cut out study area is, of course, saved and utilized as the first temporal reference cast. The remainder of the mother cast is saved and utilized as a template for further casting operations on the face of the patient. The original mother cast will be initially covered with a release agent such as petroleum jelly and then placed down onto the same position on the patient's face with the hole where the cut out area of interest had been removed now being remolded at this later time with a second cast of silastic elastomer. Care is taken to achieve an equivalent thickness with the new casting material as referenced to the surrounding mother cast. Since the mother cast is automatically accurately positioned on the surface of the skin, the cut out area in which the second and later casts are then poured and formed will also be accurately positioned as against the original cut out area of interest.

Although the discussion hereinabove has related almost exclusively to negative casts being formed of the silastic elastomer, it should be realized that positive casts may then be taken of these negative casts and utilized equivalently. Also, the needle jigs which serve to establish a common reference coordinate system between the casts taken at different times of the area of interest may be conveniently utilized with either the negative or positive molds. Thus, if the needles in the jig are inserted through both casts at the time the secondary cast is formed from the primary cast (the negative cast), the jig will serve to transfer coordinates and reference points to the secondary cast.

It has also been found that it is inconvenient to take the measurements directly from the molds which are formed from the skin surface. It is more accurate to translate the conformal molds which are curved to fit the contours of the skin surface into a flat condition by forming a further mold. This is done by first protecting the surface of the study replica by tape and then forming a new cast on top of this reference surface in a vented pressurized mold. This new cast, called the measurement cast, is formed so that the surface to be studied is hydraulically flattened in the sense that the underlying reference frame from which the measurements of the contours of the surface and the measurements casts are taken is now flat rather than curved as it was in the originally formed casts.

Once the measurement casts have been made of the study area of the skin surface taken at the different times, the commonly referenced measurement casts will then be analyzed by the optical system which provides accurate X, Y, Z coordinate values for a network of points on the surface of the measurement cast. A variety of systems are available for such measurements. An automatic focusing microscope has been used to particular advantage.

The autofocusing microscope which is utilized to record the spatial coordinates of the grid points on the specimen cast surface is shown in block schematic form in FIG. 7. Other optical measurement systems are possible, and this particular illustrated system is only one of several which could be employed. In brief, the illustrated autofocusing system utilizes a relatively low power laser beam which is caused to strike the steady surface from above at an angle of about 90°. Before the beam hits the surface, it is defocused by a lens. The lens will cause the beam to converge to a point of minimum radius equal to the focal length of the system and to diverge and expand in radius beneath that point. The position of the specimen is raised or lowered by the mechanical stage to bring the surface to the in-focus point. Once this is achieved, the vertical position of the surface is recorded as well as the horizontal X and Y coordinates. For the next measurement, the specimen mechanical stage would be moved laterally to a new grid position and the vertical position would be readjusted as necessary. Turning to the specific system illustrated in FIG. 7, the laser beam 46 is generated by a low power helium neon laser 44. The beam is initially reflected by a mirror 45 into a beam splitter 48. One portion of the beam then passes through the lens 50 and there down to the specimen 52 which is mounted on the mechanical stage 54. The other half of the beam 46 is then transferred further into the system where it passes through another beamsplitter 56 with one leg of the beam going down into the operator's optical system 60 which is served by the binocular microscope head 58. The other leg of the beam terminates in the photodetector head for the autofocusing microscope 62 which senses the timing of the achievement of the minimum spot size as the mechanical stage 54 shifts the position of the specimen in the laser beam. Messages from the autofocus system 62 are transmitted to control circuitry 66 over the line 64. This control circuitry 66 sends commands to the mechanical stage 54 over the line 70 to control the motion of the stage. The control circuitry itself is slaved to a computer 74 and receives its instructions therefrom over the line 78. A digital readout is provided to an operator over the display 72 which is accessed by the computer over line 80 and by the control circuitry 66 over line 76. Power is supplied to the system from power supply 40 the the laser 44 over power line 42 and to the control circuitry over line 68.

The specimen in such systems is mounted on a mechanical stage 54 which can move in three directions and is moved at predetermined and known distances in the horizontal plane between measurements according to a predetermined grid spacing. The distances moved in the horizontal plane can vary from as little as 25 microns. At each measurement point, the automatic focusing microscope projects a beam 46 onto the studied surface 52 which is about 5 microns in diameter. When the beam on the surface is brought into focus, the position of the point is recorded in all three dimensions, that is, X and Y in the horizontal plane and Z in the vertical plane. It is then possible to plot the position of each measured point with respect to those of all other measured points on the surface that is being studied. The grid spacing is, of course, adjustable to the degree of precision desired by the practitioner. The data obtained may then be operated upon by a variety of different algorithms to produce the quantitative model of interest to the practitioner.

The quantitative models normally will be either to analyze the roughness of the surface itself or to analyze the volumetric changes which occur over time as a result of treatments to the surface. For a regional analysis of the surface itself, a statistical analysis of the measured surface points may be done. The measured points on the surface are arrayed in lines which may be called plotting sweeps. Each of the measured points is separated by a known preselected interval which can vary according to the operator's choice. Each of the plotting sweeps is separated from an adjacent sweep by an interval identical to that separating the measured points within the line for a normal square grid system. A linear least regression analysis is made for each plotting sweep and the line of best fit is calculated therefore. The standard error of the deviation of the plotted points from that best fit line is calculated for each plotting sweep. The standard error for all of the plotting sweeps is then calculated and then may be used as an index of the roughness or smoothness of the surface. A perfectly smooth surface would have a perfectly smooth plot with a standard error of zero. This roughness value may then be compared as between different casts taken at different times of the same area to measure surface changes effects.

For volumetric analyses, it is possible by rather straightforward calculation techniques to calculate individual volumetric elements for each of the grid elements by referencing the surface coordinates to a buried datum plane from which the volumetric calculations may be conducted. In this manner, volumetric changes in isolated area or of the entire area of the measurement cast may be calculated.

What is claimed is:

1. A process for measuring changes in topology of the skin surface comprising:
   forming a dimensionally stable first replica of the topology of a skin surface at a first time, the replica being referenced to at least two stable anatomic locations on the skin surface;
   forming further replicas of the topology of the skin surface at at least one later time also referenced to the at least two stable anatomic locations; and
   measuring dimensional differences between the first and further replicas with the replicas commonly referenced such that a quantitative model of the changes in the topology of the skin surface may be made.

2. The process of claim 1 wherein the measurement of the dimensional differences is conducted with an automatically focusing apparatus which surveys the relative elevation of a network of points on the surface of the replica.

3. The process of claim 2 wherein the automatically focusing apparatus automatically scans the network of points on a preset grid having a standard grip space interval.

4. The process of claim 1 wherein the model measures the relative roughness of the surface as a function of the statistical variation in elevation of the surface as compared to a perfectly smooth surface.

5. The process of claim 1 wherein the model measures changes in volume at portions of the surface as the elevation of the portions changes over time.

6. The process of claim 1 wherein the replicas are commonly referenced by fixing the replicas to a jig means which is keyed to at least two permanent features common to each of the replicas.

7. The process of claim 1 wherein the replicas are commonly referenced by forming a first large mother cast of the skin surface of interest and surrounding tissue, then cutting out the first replica from the mother cast, and then using the cut out mother cast as a mold template for the formation of the further replicas such that the first and further replicas are commonly referenced to the cut out mother cast.

8. The process of claim 1 wherein the forming of the replicas comprises first forming a negative cast of the skin surface with a silastic elastomer, then conforming the reverse side of the negative cast to a flat surface and forming a measurement cast from the flattened negative cast such that the dimensional differences are taken from the measurement casts.

9. The process of claim 8 wherein both the negative and measurement casts are commonly referenced by fixing the negative cast to a jig means comprising a plurality of needles attached to a stable base such that at least some of the needles pass through permanent features in the negative cast and then fixing the measurement cast to the same jig by passing the same needles through the permanent features in the measurement cast.

10. The process of claim 1 wherein replicas are commonly referenced by fixing said replicas on a jig means comprising a plurality of needles such that at least some of the needles pass through permanent features common to each of the replicas.

* * * * *